United States Patent [19]

Sharik et al.

[11] Patent Number: 4,860,754
[45] Date of Patent: Aug. 29, 1989

[54] ELECTRICALLY CONDUCTIVE ADHESIVE MATERIALS

[75] Inventors: Clyde L. Sharik, Trenton, N.J.; Anthony J. Berejka, Huntington, N.Y.

[73] Assignee: E. R. Squibb & Sons, Inc., Princeton, N.J.

[21] Appl. No.: 294,970

[22] Filed: Jan. 3, 1989

Related U.S. Application Data

[63] Continuation of Ser. No. 33,313, Apr. 1, 1987, abandoned.

[51] Int. Cl.$^4$ .................................................. A61B 5/04
[52] U.S. Cl. .................................... 128/640; 128/798; 128/641; 128/802; 252/500; 252/512; 252/518
[58] Field of Search ................................ 128/639-641, 128/798, 802-803, 303.13; 252/500, 512, 518, 521; 522/79, 86, 152

[56] References Cited

U.S. PATENT DOCUMENTS

| | | | |
|---|---|---|---|
| 3,357,930 | 12/1967 | Marks | 252/518 |
| 4,066,078 | 1/1978 | Berg | 128/641 |
| 4,094,822 | 6/1978 | Kater | 128/640 X |
| 4,141,366 | 2/1979 | Cross, Jr. et al. | 128/640 |
| 4,226,247 | 10/1980 | Hauser et al. | 128/798 X |
| 4,273,135 | 6/1981 | Larimore et al. | 128/640 |
| 4,274,420 | 6/1981 | Hymes | 128/641 |
| 4,391,278 | 7/1983 | Cahalan et al. | 128/640 |
| 4,406,827 | 9/1983 | Carim | 128/639 X |
| 4,524,087 | 1/1985 | Engel | 128/639 X |
| 4,554,924 | 11/1985 | Engel | 128/798 X |
| 4,600,462 | 7/1986 | Watt | 604/372 X |
| 4,674,512 | 6/1987 | Rolf | 128/640 |
| 4,692,273 | 9/1987 | Lawrence | 128/640 X |
| 4,706,680 | 11/1987 | Keusch et al. | 128/640 |

FOREIGN PATENT DOCUMENTS

| | | | |
|---|---|---|---|
| 3133434 | 3/1983 | Fed. Rep. of Germany | 128/639 |
| 0055132 | 4/1982 | Japan | 128/639 |
| 0022625 | 1/1987 | Japan | 128/639 |

*Primary Examiner*—Kyle L. Howell
*Assistant Examiner*—Angela D. Sykes
*Attorney, Agent, or Firm*—Theodore R. Furman, Jr.

[57] ABSTRACT

Electrically conductive adhesive material possessing good adhesive, cohesive, elastomeric and conductive properties is disclosed. The present adhesive material also has improved electrical stability since it is less susceptible to drying out in most ambients. The material comprises a plasticizer, a high molecular weight water-soluble polymer, uncrosslinked polyvinylpyrrolidone as the tackifier, and an electrolyte dopant.

28 Claims, 1 Drawing Sheet

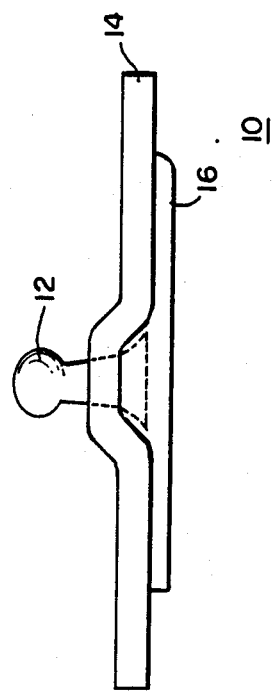

ELECTRICALLY CONDUCTIVE ADHESIVE MATERIALS

This is a continuation-in-part of co-pending application Ser. No. 033,313, filed on Apr. 1, 1987 abandoned.

FIELD OF THE INVENTION

The present invention relates to electrically conductive adhesive materials and more particularly concerns such materials suitable for use with biomedical electrodes.

BACKGROUND OF THE INVENTION

Electrically conductive adhesive materials are widely used in various biomedical applications. These materials are employed on biomedical electrodes, ground plates, and the like to establish an electrical connection between the skin of the human anatomy and an electromedical apparatus. Specifically, conductive adhesive material are used on electrodes for electromyographs, electrocardiographs, TENS (transcutaneous electrical nerve stimulation) systems, on ground plates for electrosurgery, and the like.

U.S. Pat. No. 4,066,078 to Berg describes conductive adhesives comprising an organic polymer plasticized with a polyhydric alcohol, wherein the polymer is derived from an ester of an olefinically unsaturated carboxylic acid and an alcohol having a quaternary ammonium group, or is derived from a sulfated cellulose ester.

Larimore et al., in U.S. Pat. No. 4,273,135, describe disposable biomedical electrodes having a conductive material which has no salt added for conductivity. The Larimore et al. material is a film forming, hydrophilic polymer selected from: (a) non-ionic water soluble polymers of substantially all water-soluble monomers; (b) non-ionic water soluble interpolymers of water-soluble monomers and water-insoluble monomers; or, (c) non-ionic hydrophilic water-insoluble interpolymers of water-soluble monomers and water insoluble monomers containing at least 15 mole percent of interpolymerizable water-soluble monomers. Preferred polymers from class (a) include polyvinylalcohol, polyvinylpyrrolidone, polyacrylic acid and the like. Preferred interpolymers from class (b) include copoly(vinylacetate:vinylalcohol) and copoly(n-butyl acrylate:acrylic acid). Preferred interpolymers from class (c) include copoly(vinylchloride:vinylalcohol). Larimore et al. suggest that the addition of tackifiers to their formulations is necessary in most cases to obtain good adhesive qualities. For example, the Larimore et al. formulations based on polyvinyl-alcohol and glycerin (with no additional tackifiers) were found to be non-tacky.

In U.S. Pat. No. 4,391,278, Cahalan et al. describe a conductive adhesive comprised of a polymerized form of 2-acrylamido-2-methyl-propansulfonic acid with water or an alcohol, e.g. glycerol. Cahalan et al. disclose that optional thickeners, such as polyvinylpyrrolidone, polyvinylalcohol, karaya gum, and xanthan gum, may be employed with their acid polymer composition.

U.S. Pat. No. 4,094,822 to Kater describes a biomedical electrode which makes electrical and physical contact to the skin by dispersing a metal salt, e.g. silver chloride, throughout an adhesive which is preferably 15 to 25 percent polyvinylalcohol (88% hydrolyzed form), 5 to 7.5 percent boric acid, 1.5 to 2.5 percent carboxymethylcellulose, 5 to 10 percent glycerol and the balance water. The conductivity of these and most other adhesive formulations is dependent on a relatively stable water content. Since the adhesive of Kater typically contains 55 to 70 percent by weight of water, special packaging is required to maintain that water content. Formulations having this much water are likely to partially dry out in ambient conditions, thereby adversely affecting the electrical and elastomeric properties.

Engel, in U.S. Pat. No. 4,554,924, describes a conductive adhesive prepared by forming an adhesive precursor on the electrode and thereafter polymerizing the precursor in situ. The conductive adhesive precursor comprises a water soluble polyhydric alcohol which is liquid at about 20° C.; at least one non-ionic unsaturated free radically polymerizable material soluble in said polyhydric alcohol; a free radical initiator soluble in said polyhydric alcohol; a cross-linking agent of a multifunctional unsaturated free radically polymerizable material soluble in said polyhydric alcohol; and, an ionizable salt in an amount effective to render said adhesive product electrically conductive. The polyhydric alcohol can be glycerol and the polymerizable material is preferably acrylic acid, methacrylic acid, N-vinyl-pyrrolidone and the like. The initiator can be, for example, benzoyl peroxide; the cross-linking agent is preferably TEGBM (triethylene-glycol-bis-methacrylate), and the ionizable salt is typically an inorganic halide, preferably an inorganic chloride. These adhesives also may contain about 10 percent by weight of water.

SUMMARY OF THE INVENTION

In accordance with the present invention an improved electrically conductive adhesive material is disclosed. The conductive adhesive suitable for use with, for example, biomedical electrodes comprises a low molecular weight plasticizer selected from alcohols and polyhydric alcohols; a high molecular weight water soluble, cross-linkable polymer, which is also soluble in said plasticizer; uncrosslinked polyvinylpyrrolidone in an amount sufficient to tackify the plasticizer and polymer; and, an electrolyte dopant in an amount sufficient to render the adhesive material electrically conductive.

BRIEF DESCRIPTION OF THE DRAWING

FIG. 1 is a cross-sectional view of an electrode using the conductive adhesive of the invention.

DETAILED DESCRIPTION OF THE INVENTION

The electrically conductive adhesive material of the present invention is suitable for use in any of the biomedical electrodes known in the art, such as those illustrated in the patents discussed above. Referring to the FIGURE, a typical biomedical electrode 10 comprises an electrode plate 12 (which may be a plate probe or element) integral with a backing layer 14 of a web-like or foam-like material as known in the art. The backing layer 14 is typically larger in diameter than the electrode plate 12 so as to provide a relatively broad area of contact with the skin for electrical and adhesive purposes. As shown in the FIGURE, the electrode plate 12 may actually extend through the backing layer 14. The electrically conductive adhesive material 16 is contacted to that side of the backing layer 14 which is to be directed to the skin. The electrode 10 may optionally include a conductive film (not shown) interposed the backing layer 14 and the conductive adhesive 16 as known in the art. Alternatively, the backing layer 14 may be a conductive film. While the FIGURE illustrates one type of biomedical electrode, it should be apparent that other electrode designs and any application requiring electrically conductive adhesive materials would be benefited by the present invention.

The electrically conductive adhesive material of the present invention is advantageous in that it functions as a highly flexible, elastomeric gel-like substance with excellent electrical, cohesive and adhesive properties while having a water content of about 10 to 20 percent by weight or less in a preferred embodiment. In general, the conductivity, and often the elastomeric properties, of these types of material are highly dependent on the amount of water formulated into the material. Prior art materials which rely upon a high water content (e.g. 50 weight percent and above) are typically susceptible to drying out in most ambients. To prevent possible loss of conductivity and /or elastomeric properties, stringent packaging and storing are necessary when using these prior art materials. Since materials containing about 20 percent by weight of water are less subject to drying out, more stable, electrically conductive adhesive materials are provided by the present invention.

Polyvinylpyrrolidone is an ingredient found in prior art conductive adhesives as a basic polymer around which the composition is built, or as a thickening agent. Such compositions in which polyvinylpyrrolidone is the basic polymer typically include a tackifier, such as abietic acid and the like, to impart adhesive qualities to the material. Unexpectedly, polyvinylpyrrolidone in combination with polymer/plasticizer blends otherwise known to require a tackifying agent produces a gel-like polymeric substance with excellent adhesive and cohesive properties.

These prior art uses of polyvinylpyrrolidone utilize the cross-linked form of the polymer which gives it the desired properties. Unexpectedly, it has been found that uncrosslinked polyvinylpyrrolidone functions well as a tackifying agent in the compositions of the present invention.

The conductive adhesive of the present invention includes a low molecular weight plasticizer selected from alcohols and polyhydric alcohols. The alcohols suitable for use as the plasticizer should be relatively non-volatile at room temperature, i.e. they should have a vapor pressure higher than that of water. Typical alcohols include isooctylalcohol, decanol and the like. Polyhydric alcohols suitable for use as the plasticizer include polyethylene glycol, methoxy polyethylene glycols, propylene glycol, higher alkyl glycols and glycerin, with the latter being preferred. The plasticizer preferably has a molecular weight of less than about 4000. The low molecular weight plasticizer is typically present in an amount of from about 40 to 92 percent by weight, and preferably from about 50 to 70 percent by weight of the total adhesive material.

The high molecular weight water soluble polymer must be susceptible to chemical and/or ionic cross-linking and must also be soluble in said plasticizer. The cross-linking (of one type or the other) gives the desired viscosity to the adhesive. Polymers suitable typically have a molecular weight above 4000 and include gelatin, polyethylene oxides, and polyvinylalcohols. Polyvinylalcohols having a molecular weight of between about 20,000 and 108,000 are preferred and polyvinylalcohol which is about 88% hydrolyzed having a molecular weight of about 78,000 is most preferred because of the excellent flexibility it imparts to the conductive adhesive. The high molecular weight polymer is typically present in an amount of from about 2 to 54 percent by weight, and preferably from about 2 to 10 percent by weight of the total adhesive material.

The uncrosslinked polyvinylpyrrolidones suitable for use in the present invention have a molecular weight between about 10,000 and 360,000 with 10,000 being preferred. The uncrosslinked polyvinylpyrrolidone should be present in an amount of from about 1 to about 53 percent by weight, and preferably from about 5 to 30 percent by weight of the total adhesive material.

The electrolyte dopant of the present invention may be any organic or inorganic ionizable salt which will provide the desired conductivity and does not interfere with the physical properties of the adhesive. For use on electrocardiograph electrodes, the salt must also be capable of recovering rapidly following defibrillation overload. Inorganic ionizable salts, particularly inorganic halide salts are well-suited as electrolyte dopants for the present invention. The salts can be monovalent such as sodium chloride or potassium chloride or polyvalent such as magnesium chloride with the latter being preferred. The polyvalent salts such as magnesium chloride are preferred as the electrolyte dopant because they can ionically cross-link numerous of the high molecular weight, water-soluble polymers, such as the polyvinylalcohols, described above. When the polyvalent-salts, such as magnesium chloride serve the dual function of electrolyte and cross-linking agent, the further addition of a cross-linking agent is optional. The electrolyte dopant is typically present in an amount of from about 5 to about 57 percent by weight, and preferably from about 10 to 35 percent by weight of the total adhesive.

The electrolyte dopant may also contain water. For example, the preferred dopant is typically in hydrated form, i.e. magnesium chloride hexahydrate ($MgCl_2 \cdot 6H_2O$) which is approximately 50 percent by weight of water. Additionally the hydrated or nonhydrated salts used as the electrolyte may be in an aqueous solution. For those dopants containing water (i.e. salts which are hydrated and/or in aqueous solution), the salt to water weight ratio should be from about 1:1 to about 1:40. For example, in one embodiment the dopant is an aqueous solution comprising 20 weight percent of magnesium chloride hexahydrate (consisting of 10 weight percent $MgCl_2$ and 10 weight percent water) in 10 weight percent of water. Such a dopant composition is illustrative of the preferred 1:2 salt to water ratio for the electrolyte of the present invention.

Alternatively, water can be added, as necessary for conductivity, viscosity, etc., independent of the dopant. In any case, the total water in the conductive adhesives of the present invention is typically up to about 40 percent by weight and preferably from about 10 to about 20 percent by weight of the total adhesive.

In accordance with the present invention, when the electrolyte dopant comprises a monovalent salt, i.e. a salt which does not ionically cross-link the high molecular weight polymer, a cross-linking agent should be added to enhance the viscosity of the material. Typical chemical cross-linking agents include boric acid, sodium borate, and the like which may be present in an amount of from about 0.1 to about 5 percent by weight of the total adhesive. The cross-linking agent may be in hydrated form or may be included by way of solution.

In all cases, it is understood that any of the cross-linking agents employed will not cross-link the polyvinylpyrrolidone and irradiative cross-linking methods are avoided.

To prepare the electrically conductive adhesives of the present invention, conventional mixing machines can be used to combine the ingredients, for example, those manufactured by Brabender, Charles Ross & Son, and the like. In some cases it may be desirable to use a mixer capable of operating under vacuum to eliminate voids in the resultant material. In a typical preparation, the plasticizer such as glycerin is put into the mixer and while mixing, the polyvinylpyrrolidone and the high molecular weight polymer, such as polyvinylalcohol, are added. After mixing these components (typically at room temperature) for 5-15 minutes, heat is applied so that further mixing takes place at between about 90° and 120° C. Once these components have been stirred for about 15 minutes at temperature, the electrolyte dopant and cross-linking agent (if used) are added slowly. These two ingredients can be added in crystal form or in solution. Following the dopant and cross-linking agent additions, the total formulation is mixed under somewhat reduced heat (70°-90° C.) for another 5-10 minutes, then dumped and allowed to cool.

By adjusting the proportions of the components, numerous adhesive materials of varying conductivity and flexibility can be obtained within the scope of the present invention. The adhesive materials of this invention are not only readily adapted for the less demanding high impedance ground plate and TENS electrode area, but are also well within the stringent, industry-accepted AAMI (Association for the Advancement of Medical Instrumentation) standards for electrocardiograph electrodes. Additionally, the electrocardiograph electrodes have extremely low noise values.

The present invention will now be described by referring to the following examples, however, the invention is not meant to be limited by the details described therein.

EXAMPLE 1

An electrically conductive adhesive material in accordance with the present invention was prepared using the following ingredients by the procedure described below.

| Ingredient | Weight Percent |
| --- | --- |
| Glycerin | 55.5 |
| Polyvinylalcohol (Vinol S-523; 88% hydrolyzed; M.W. 78,000; avail. from Air Products) | 4.5 |
| Polyvinylpyrrolidone (PVP K-15; M.W. 10,000; avail. from GAF) | 9.0 |
| Magnesium chloride hexahydrate ($MgCl_2.6H_2O$) | 20.0 |
| Water | 10.0 |
| Sodium borate decahydrate ($Na_2B_4O_7.10H_2O$) | 1.0 |

The glycerin (222 g) was poured at room temperature into a mixing apparatus and mixed at about 190 RPM while the polyvinylpyrrolidone (36 g) and then the polyvinylalcohol (18 g) were added. These three components were mixed for about 5 minutes. While the mixing continued the so-formed mixture was heated to between about 100° and 120° C. After about 15 minutes of mixing at this temperature, 44 g of a 1:10 solution of the sodium borate decahydrate in water was slowly added followed by the addition of magnesium chloride hexahydrate crystals (80 g). These two additions were spread out over about 10 minutes of mixing during which time the temperature was allowed to drop to about 90° C. The mixing was then continued for another 5 minutes, then dumped. When allowed to cool, the mixture took on a flexible, elastomeric gel-like consistency which had good adhesive and cohesive properties.

When the so-formed adhesive was later tested on an AAMI (Association for the Advancement of Medical Instrumentation) electrocardiograph electrode test apparatus, it was found to have an initial 305 ohm impedance at a frequency of 10 Hz, and a more than satisfactory 210 ohm impedance after defibrillation recovery. The complete AAMI test data for this adhesive is listed below.

| | DC Offset Millivolts | AC Imped. ohms | Defibrillation Overload Recovery | | Subsequent Impedance ohms | Internal Noise Microvolts |
| --- | --- | --- | --- | --- | --- | --- |
| | | | DC Offset | Slope | | |
| AAMI Specif. | <100 mv | <2000 ohms | <100 mv | <1 mv/sec | <3000 ohms | <150 μv |
| Example 1 | 0.6 mv | 305 ohms | 27.2 mv | 0.4 mv/sec | 210 ohms | 11.0 μV |

EXAMPLE 2

Using the procedure of Example 1, an electrically conductive adhesive material suitable for ground plate electrodes for electrosurgery or for TENS electrodes, were prepared. This material contained the ingredients listed below.

| Ingredient | Weight Percent |
| --- | --- |
| Glycerin | 50 |
| Gelatin | 15 |
| Polyvinylpyrrolidone (PVP K-90; M.W. 360,000; avail. from GAF) | 15 |
| Magnesium chloride hexahydrate ($MgCl_2.6H_2O$) | 10 |
| Water | 10 |

As opposed to the 10 Hz frequency range for Example 1, this material was tested in the 500 KHz to 2 MHz frequency range and found to have a volume resistivity of $10^3$ ohm-cm.

EXAMPLE 3

Using the procedure of Example 1, a conductive adhesive suitable for an electrocardiograph electrode was prepared using a pre-gelled (i.e. pre-borated by the manufacturer) polyvinylalcohol.

| Ingredient | Weight Percent |
| --- | --- |
| Glycerin | 50 |
| Polyvinylalcohol (Vinol MM-Sl; M.W. 78,000; pre-gelled; avail. from Air Products) | 3 |
| Polyvinylpyrrolidone (PVP K-15; M.W. 10,000; avail. from GAF) | 7 |
| Magnesium chloride hexahydrate ($MgCl_2.6H_2O$) | 20 |
| Water | 20 |

At a frequency of 10 Hz, the so-formed material had an impedance value of 250 ohms as per the AAMI test apparatus.

EXAMPLES 4–8

The following additional adhesive materials within the scope of the present invention were prepared using the procedure of Example 1.

| Ingredient | Weight Percent | | | | |
| --- | --- | --- | --- | --- | --- |
| | Ex. 4 | Ex. 5 | Ex. 6 | Ex. 7 | Ex. 8 |
| Glycerin | 47 | 48.5 | 47 | 52.2 | 47 |
| Polyvinylalcohol (as in Ex. 1) | 4.0 | 3.5 | 4.0 | 4.4 | 4.0 |
| Polyvinylpyrrolidone (as in Ex. 1) | 8.0 | 7.0 | 8.0 | 8.9 | 8.0 |
| Magnesium chloride hexahydrate ($MgCl_2 \cdot 6H_2O$) | 20.0 | 20.0 | 20.0 | 22.2 | 30.0 |
| Water | 20.0 | 20.0 | 20.0 | 11.1 | 10.0 |
| Sodium borate decahydrate ($Na_2B_4O_7 \cdot 10H_2O$) | 1.0 | 1.0 | 1.0 | 1.1 | 1.0 |

Upon testing these materials at 10 Hz, as in Example 1, the following impedance values were obtained.

| Ex. No. | Impedance | |
| --- | --- | --- |
| | Initial | After Defib. Recovery |
| 4 | 215 ohms | 175 ohms |
| 5 | 256 ohms | 200 ohms |
| 6 | 170 ohms | 120 ohms |
| 7 | 245 ohms | 205 ohms |
| 8 | 270 ohms | 200 ohms |

What is claimed is:

1. An electrically conductive adhesive material comprising:
    a low molecular weight plasticizer selected from non-volatile alcohols and polyhydric alcohols;
    a high molecular weight, water soluble, cross-linkable polymer which is also soluble in said plasticizer;
    a tackifier comprising uncrosslinked polyvinylpyrrolidone; and
    an electrolyte dopant in an amount sufficient to render said adhesive material electrically conductive.

2. The material of claim 1 wherein said plasticizer is present in an amount of from about 40 to about 92 percent by weight of the total adhesive material.

3. The material of claim 2 wherein said plasticizer is present in an amount of from about 50 to about 70 percent by weight of the total adhesive material.

4. The material of claim 1 wherein said plasticizer comprises a polyhydric alcohol having a molecular weight of about 4000 or less selected from polyethylene glycols, methoxy polyethylene glycols, propylene glycol, higher alkyl glycols and glycerin.

5. The material of claim 1 wherein said high molecular weight polymer is present in an amount of from about 2 to about 54 percent by weight of the total adhesive material.

6. The material of claim 5 wherein said high molecular weight polymer is present in an amount of from about 2 to about 10 percent by weight of the total adhesive material.

7. The material of claim 1 wherein said high molecular weight polymer has a molecular weight in excess of about 4000.

8. The material of claim 1 wherein said high molecular weight polymer is selected from gelatin, polyvinylalcohols and polyethylene oxides.

9. The material of claim 8 wherein said high molecular weight polymer comprises a polyvinylalcohol having a molecular weight of between about 20,000 and about 108,000.

10. The material of claim 9 wherein said high molecular weight polymer is polyvinylalcohol having a molecular weight of about 78,000.

11. The material of claim 1 wherein said polyvinylpyrrolidone is present in an amount of from about 1 to about 53 percent by weight of the total adhesive material.

12. The material of claim 11 wherein said polyvinylpyrrolidone is present in an amount of from about 5 to about 30 percent by weight of the total adhesive material.

13. The material of claim 1 wherein said polyvinylpyrrolidone has a molecular weight of from about 10,000 to about 360,000.

14. The material of claim 13 wherein said polyvinylpyrrolidone has a molecular weight of about 10,000.

15. The material of claim 1 wherein said electrolyte dopant is present in an amount of from about 5 to about 57 percent by weight of the total adhesive material.

16. The material of claim 15 wherein said electrolyte dopant is present in an amount of from about 10 to about 35 percent by weight of the total adhesive material.

17. The material of claim 1 wherein said electrolyte dopant comprises an ionizable monovalent or polyvalent salt, and further wherein said polyvalent salt can also serve as a crosslinking agent for said high molecular weight water soluble, crosslinkable polymer.

18. The material of claim 17 wherein said dopant is a monovalent salt selected from sodium chloride, potassium chloride and silver chloride.

19. The material of claim 17 wherein said dopant is a polyvalent salt which may be hydrated selected from magnesium chloride, magnesium acetate, zinc chloride, zinc acetate, calcium chloride and ferric chloride.

20. The material of claim 17 further comprising a cross-linking agent selected from boric acid and sodium borate.

21. The material of claim 1 further comprising water.

22. The material of claim 21 wherein the total water content is about 40 percent by weight or less of the total adhesive material.

23. The material of claim 22 wherein the total water content is from about 10 to about 20 percent by weight of the total adhesive material.

24. The material of claim 21 wherein said salt is in a hydrated form and/or in an aqueous solution.

25. The material of claim 24 wherein said salt and water are present within the electrolyte dopant in a salt-to-water weight ratio of between about 1:1 and about 1:40.

26. The material of claim 25 wherein said salt-to-water weight ratio is about 1:2.

27. The material of claim 1 comprising in a homogeneous combination:
    about 55 percent by weight of glycerin;
    about 5 percent by weight of an 88% hydrolyzed, crosslinked polyvinylalcohol having a molecular weight of about 78,000;
    about 9 percent by weight of an uncrosslinked polyvinylpyrrolidone having a molecular weight of about 10,000;
    about 1 percent by weight of sodium borate decahydrate;

about 20 percent by weight of magnesium chloride hexahydrate; and about 10 percent by weight of water exclusive of the water contained in said magnesium chloride hexahydrate.

28. In a biomedical electrode suitable for establishing an electrical connection between the skin of the human anatomy and an electromedical apparatus, said biomedical electrode comprising an electrode plate, probe or element electrically connected to said electromedical apparatus; a backing layer integral with, and having a larger diameter than, said electrode plate; and, an electrically-conductive adhesive means contacted to a major surface of said backing layer which is to contact said skin, which adhesive means maintains physical and electrical contact between said electrode plate, probe or element and said skin, the improvement wherein said electrically-conductive adhesive means comprises a low molecular weight plasticizer selected from non-volatile alcohols and polyhydric alcohols;

a high molecular weight, water soluble, cross-linkable polymer which is also soluble in said plasticizer;

a tackifier comprising uncrosslinked polyvinylpyrrolidone; and, an electrolyte dopant in an amount sufficient to render said adhesive material electrically conductive.

* * * * *